United States Patent [19]

Krauss

[11] Patent Number: 5,602,143

[45] Date of Patent: Feb. 11, 1997

[54] METHOD FOR REDUCING INTRAOCULAR PRESSURE IN THE MAMMALIAN EYE BY ADMINISTRATION OF GUANYLATE CYCLASE INHIBITORS

[75] Inventor: Achim H. Krauss, Irvine, Calif.

[73] Assignee: Allergan, Waco, Tex.

[21] Appl. No.: 352,018

[22] Filed: Dec. 8, 1994

[51] Int. Cl.$^6$ ..................................................... A61K 31/44
[52] U.S. Cl. ........................... 514/299; 514/912; 514/913
[58] Field of Search ..................................... 514/299, 912, 514/913

[56] References Cited

U.S. PATENT DOCUMENTS 4,757,089  7/1988  Epstein .

FOREIGN PATENT DOCUMENTS

WO88/05306  7/1988  WIPO .
WO93/23052  11/1993  WIPO .

OTHER PUBLICATIONS

Korenfeld et al, "Atrial Natriuretic Peptides", Invest. Ophthalm. Visual Sci., vol. No. 11, 1989, pp. 2385–2392.

J. A. Nathanson, "Nitrovasodilators as a New Class of Ocular Hypotensive Agents", J. Pharmacol. Exp. Ther., vol. 260, No. 3, 1992, pp. 956–965.

Krupin et al, "Increased intraocular pressure following topical azide or nitroprusside", Invest. Ophthalm. Vis. Sci., vol. 16, No. 11, 1977, pp. 1002–1007.

The Journal of Pharmacology and Experimental Therapeutics, vol. 247, No. 1, pp. 283–288,1988,Mulsch et al. "LY 83583 Interferes with the Release of Endothelium–Derived Relaxing Factor and Inhibits Soluble Guanylate Cyclase".

The Journal of Pharmacology and Experimental Therapeutics, vol. 232, No. 3, pp. 764–769, 1985, Schmidt et al, "LY83583: An Agent That Lowers Intracellular Levels of Cyclic Guanosine 3',5'-Monophosphate[1] ".

Eur. J. Biochem., vol. 116: 479–486, 1981, Gerzer et al, "Purification of a Soluble, Sodium–Nitroprusside–Stimulated Guanylate Cyclase From Bovine Lung".

Eur. J. Pharmacol, vol. 135, pp. 247–250, 1987, Mulsch et al, "Stimulation of Soluble Guanylate Cyclase By Endothelium–Derived Relaxing Factor From Cultured Endothelial Cells".

Schultz, G. and E. Bohme, Guanylate cyclase. In: Methods of Enzymatic Analysis, 3, 379–389, 1984, Schultz et al, "GTP pyrophosphate–lyase (cyclizing), EC 4.6.1.2", ed. H. U. Bergmeyer, Verlag Chemie, Weinheim.

Primary Examiner—Zohreh Fay
Attorney, Agent, or Firm—Robert J. Baran; Martin A. Voet; Howard R. Lambert

[57]  ABSTRACT

Pharmaceutical compositions and a method are disclosed for treating glaucoma and/or ocular hypertension in the mammalian eye by administering to the mammalian eye the pharmaceutical composition of the invention which contains as the active ingredient one or more compounds having guanylate cyclase inhibition activity. Examples of guanylate cyclase inhibitors utilized in the pharmaceutical composition and method of treatment are:

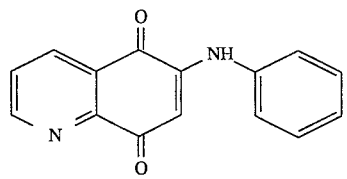

and pharmaceutically acceptable salts thereof.

5 Claims, No Drawings

METHOD FOR REDUCING INTRAOCULAR PRESSURE IN THE MAMMALIAN EYE BY ADMINISTRATION OF GUANYLATE CYCLASE INHIBITORS

BACKGROUND OF INVENTION

1. Field of the Invention

The present invention is directed to pharmaceutical compositions, and primarily to topically applied ophthalmic compositions comprising as the active ingredient one or more compounds having the ability to inhibit guanylate cyclase. The pharmaceutical compositions are useful for reducing intraocular pressure in animals of the mammalian species. In another aspect, the present invention is directed to administering such formulations and compositions to animals of the mammalian species (including humans) for reducing intraocular pressure in the eye.

2. Brief Description of the Art

Glaucoma is an optical neuropathy associated with elevated intraocular pressures which are too high for normal function of the eye, and results in irreversible loss of visual function. It is estimated in medical science that glaucoma afflicts approximately 2 percent of the population over the age of forty years, and is therefore a serious health problem. Ocular hypertension, i.e. the condition of elevated intraocular pressure, which has not yet caused irreversible damage, is believed to represent the earliest phase of glaucoma. Many therapeutic agents have been devised and discovered in the prior art for the treatment or amelioration of glaucoma and of the condition of increased intraocular pressure which precedes glaucoma.

The drugs currently utilized in the treatment of glaucoma include miotics (e.g., pilocarpine, carbachol, and acetylcholinesterase inhibitors), sympathomimetrics (e.g., epinephrine and dipivalylepinephrine), beta-blockers (e.g., betaxolol, levobunolol and timolol), alpha-2 agonists (e.g., para-amino clonidine) and carbonic anhydrase inhibitors (e.g., acetazolamide, methazolamide and ethoxzolamide). Miotics and sympathomimetics are believed to lower intraocular pressure by increasing the outflow of aqueous humor, while beta-blockers, alpha-2 agonists and carbonic anhydrase inhibitors are believed to lower intraocular pressure by decreasing the formation of aqueous humor. All five types of drugs have potential side effects. Miotics, such as pilocarpine, can cause blurring of vision and other visual side effects which may either decrease patient compliance or require termination of miotic drug therapy. Carbonic anhydrase inhibitors can also cause serious side effects which affect patient compliance and/or necessitate withdrawal of the drug therapy. At least one beta-blocker, timolol, has increasingly become associated with serious pulmonary side effects attributable to its effect on beta-2 receptors in pulmonary tissue.

As a result additional antiglaucoma drugs are being developed, e.g., prostaglandin derivatives, muscarinic antagonists, etc.

In light of the foregoing circumstances, it is clear that a need exists for new, more potent antiglaucoma compositions which avoid or reduce the above-cited side effects and enhance patient compliance. The present invention is directed to the provision of such compositions.

6-anilinoquinoline-5,8-quinone (LY 83583) was originally developed as an inhibitor of antigen-induced leukotriene release. Subsequently, it was found to be an effective agent for the lowering of cyclic GMP levels in a wide range of tissues, while having little or no effect on cyclic AMP levels. The mechanisms of its lowering action on cyclic GMP may include inhibition of endothelium-derived relaxing factor and blocking of activation of soluble guanylate cyclase.

The cyclic GMP-lowering effect of LY 83583 has been used to help elucidate the mechanisms by which atrial natriuretic factor acts on cation channel transport, and the mechanisms of muscle relaxation induced by nitrate esters.

SUMMARY OF THE INVENTION

Surprisingly it has been discovered in accordance with the present invention that guanylate cyclase inhibitors (GCIs) are effective as anti-glaucoma agents and as agents for reducing intraocular pressure, when such agents are applied to the mammalian eye in a pharmaceutical composition, preferably in a topical ophthalmic composition. Accordingly, the present invention relates to a method of treating glaucoma, or ocular hypertension by topically administering to the mammalian eye an ophthalmic composition which contain an effective amount of a GCI. A preferred example of GCI's suitable as the active ingredient of the ophthalmic compositions of the invention, are:

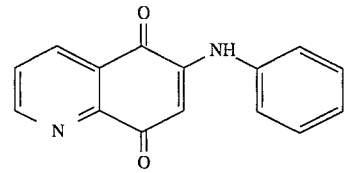

and pharmaceutically-acceptable salts thereof.

This compound is also known as 6-anilinoquinoline-5,8-quinone.

While not wishing to be bound by theory it is believed that GCI's lower IOP by increasing aqueous humor outflow facility since it has been demonstrated that compounds which contract or relax ciliary smooth muscle increase or decrease outflow facility respectively. In this context it has been shown that organic nitrates which are known activators of guanylate cyclase can decrease outflow facility in the monkey eye and that nitric oxide causes relaxation of bovine ciliary muscle in vitro. Thus, inhibition of guanylate cyclase would block any physiological relaxing stimulus on ciliary muscle exerted by nitric oxide or other mediators using cyclic GMP (cGMP) as a second messenger.

In addition, cGMP may inhibit the synthesis of arachidonic acid and ocular hypotensive prostaglandins in ocular tissues. Blockage of synthesis and release of arachidonic acid and metabolites with cell permeable, stable cGMP analogs has been shown in human platelets for example. GCI's would thereby act as indirect ocular hypotensives by increasing the availability of ocular hypotensive prostaglandins in the eye.

Glutamate and nitric oxide, previously called endothelium-derived relaxing factor EDRF, have been implicated in nerve cell damage. Nitric oxide synthase is present in neuronal tissues of the eye and can be stimulated by glutamate, a known neurotransmitter and excitotoxin. Since both nitric oxide and glutamate are known to increase levels of cGMP in the retina, treatment of ocular hypertensive and glaucomatous subjects with GCI's may prevent further loss of retinal ganglion cells and deterioration of the visual field. LY83583 in particular may have an additional beneficial effect by its direct inhibition of EDRF formation.

It has been reported that ethacrynic acid may be a guanylate cyclase inhibitor, but the data does not conclusively support this report. Moreover, ethacrynic acid is reported in (Epstein) U.S. Pat. No. 4,757,089, to increase aqueous humor outflow in the eye. However, the mechanism of this action is by irreversible chemical reaction with sulfhydryl groups in the eye. As will be appreciated by one of ordinary skill in the art, it is desirable to irreversibly change the chemical structure of the eye.

The ophthalmic compositions of the invention contain the active ingredient in a concentration range of approximately 0.0001 to 1.0 percent weight by volume. The composition itself includes, in addition to the active ingredient, such excipients which are per se well known in the art for preparing ophthalmic compositions, particularly ophthalmic solutions. In accordance with the method of the invention the ophthalmic compositions, preferably ophthalmic solutions are applied topically to the mammalian eye approximately 1 or 2 times daily.

DETAILED DESCRIPTION OF THE INVENTION

The compounds which are utilized in accordance with the method of the present invention, and in the pharmaceutical compositions of the present invention, are GCI's. In this regard the term GCI is defined as those compounds which inhibit the soluble form of the enzyme guanylate cyclase thus suppressing resting levels as well as stimulated formation of the intracellular second messenger cyclic GMP. Specific and preferred examples of GCI's which are utilized in accordance with the present invention are provided below.

LY83583 methylene blue

N-methylhydroxylamine hydroxylamine retinol

Pharmaceutically acceptable salts of the GCI's can also be used in accordance with the present invention. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, such as alkali ions, e.g. sodium, potassium, etc. Organic amine salts may be made with amines, particularly ammonium salts such as mono-, di- and trialkyl amines, e.g. alkyl amines wherein each alkyl group may comprise up to six carbon atoms, or ethanol amines. Salts may also be formed with caffeine, tromethamine and similar molecules. It is only important that the cation of any salt of a GCI utilized in the compositions or methods of this invention be able to inhibit guanylate cyclase.

For reducing intraocular pressure in a mammalian eye, and particularly for treatment of glaucoma in humans suffering from that condition, the active compounds (or mixtures or salts thereof) are administered in accordance with the present invention to the eye admixed with an ophthalmically acceptable carrier. Any suitable, e.g., conventional, ophthalmically acceptable carrier may be employed. A carrier is ophthalmically acceptable if it has substantially no long term or permanent detrimental effect on the eye to which it is administered. Examples of ophthalmically acceptable carriers include water (distilled or deionized water), saline and other aqueous media. In accordance with the invention, the active compounds are preferably soluble in the carrier which is employed for their administration, so that the active compounds are administered to the eye in the form of a solution. Alternatively, a suspension of the active compound or compounds (or salts thereof) in a suitable carrier may also be employed.

In accordance with the invention the active compounds (or mixtures or salts thereof) are administered in an ophthalmically acceptable carrier in sufficient concentration so as to deliver an effective amount of the active compound or compounds to the eye. Preferably, the ophthalmic, therapeutic solutions contain one or more of the active compounds in a concentration range of approximately 0.0001% to approximately 1.0% (weight by volume) and more preferably approximately 0.0005% to approximately 0.1% (weight by volume).

Any method of administering drugs directly to a mammalian eye may be employed to administer, in accordance with the present invention, the active compound or compounds to the eye to be treated. By the term "administering directly" is meant to exclude those general systemic drug administration modes, e.g., injection directly into the patient's blood vessels, oral administration and the like, which result in the compound or compounds being systemically available. The primary effect on the mammal resulting from the direct administering of the active compound or compounds to the mammal's eye is preferably a reduction in intraocular pressure. More preferably, the active useful compound or compounds are applied topically to the eye or are injected directly into the eye. Particularly useful results are obtained when the compound or compounds are applied topically to the eye in an ophthalmic solution, i.e. as ocular drops.

Topical ophthalmic preparations, for example ocular drops, gels or creams, are preferred because of ease of application, ease of dose delivery and fewer systemic side effects, such as cardiovascular hypotension. An exemplary topical ophthalmic formulation is shown below in Table I. The abbreviation q.s. means a quantity sufficient to effect the result or to make volume.

TABLE I

| Ingredient | Amount(% W/V) |
|---|---|
| Active Compound in accordance with the invention, (GCI) | about 0.0001 to about 1.0 |
| Preservative | 0–0.10 |
| Vehicle | 0–40 |
| Tonicity Adjustor | 1–10 |
| Buffer | 0.01–10 |
| pH Adjustor | q.s. pH 4.5–7.5 |
| antioxidant | as needed |
| Purified Water | as needed to make 100% |

Various preservatives may be used in the ophthalmic preparation described in Table I above. Preferred preservatives include, but are not limited to, benzalkonium chloride, chlorobutanol, thimerosal, phenylmercuric acetate, and phenylmercuric nitrate. Likewise, various preferred vehicles may be used in such ophthalmic preparation. These vehicles include, but are not limited to, polyvinyl alcohol, povidone, cyclodextrines, hydroxypropyl methyl cellulose, poloxamers, carboxymethyl cellulose and hydroxyethyl cellulose.

Tonicity adjustors may be added as needed or convenient. They include, but are not limited to, salts, particularly sodium chloride, potassium chloride etc., mannitol and glycerin, or any other suitable ophthalmically acceptable tonicity adjustor.

Various buffers and means for adjusting pH may be used so long as the resulting preparation is ophthalmically acceptable. Accordingly, buffers include but are not limited to, acetate buffers, citrate buffers, phosphate buffers, and borate buffers. Acids or bases may be used to adjust the pH of these formulations as needed.

In a similar vein, ophthalmically acceptable antioxidants include, but are not limited to, sodium metabisulfite, sodium thiosulfate, acetylcysteine, butylated hydroxyanisole, and butylated hydroxytoluene.

The ophthalmic solution (ocular drops) may be administered to the mammalian eye as often as necessary to maintain an acceptable level of intraocular pressure in the eye. In other words, the ophthalmic solution (or other formulation) which contains the GCI agent as the active ingredient, is administered to the mammalian eye as often as necessary to maintain the beneficial hypotensive effect of the active ingredient in the eye. Those skilled in the art will recognize that the frequency of administration depends on the precise nature of the active ingredient and its concentration in the ophthalmic formulation. Within these guidelines it is contemplated that the ophthalmic formulation of the present invention will be administered to the mammalian eye approximately once or twice daily.

Preferred examples of GCI's which are used as the active effective ingredients in the ophthalmic compositions of the present invention are described and shown below:

LY83583 methylene blue ethacrynic acid

N-methylhydroxylamine hydroxylamine retinol

Alternatively, GCI's may be defined as a pharmaceutical compound showing activity in the following assay: Soluble guanylate cyclase (GC) was purified from bovine lung with a modification of a procedure disclosed in Gerzer et al, "Purification of a soluble, sodium-nitroprusside-stimulated guanylate cyclase from bovine lung" Eur. J. Biochem. 116: 479–486, 1981. In this assay, Zeta prep DEAE 3200 cartridges (CUNO Europe, Mainz, FRG), Sepharose CL-2B (Pharmacia, Freiburg, FRG) containing 1 µmol/ml of covalently coupled reactive blue and a modified version of the polyacrylamide-gel-electrophoresis device (System Havanna, Desaga, Heidelberg, FRG) are used.

For the detection of endothelium-derived relaxing factor (EDRF) by direct activation of soluble GC as disclosed in Mulsch et al, "Stimulation of soluble guanylate cyclase by endothelium-derived relaxing factor from cultured endothelial cells", Eur. J. Pharmacol. 135; 247–250, 1987, the effluent of an endothelial cell column was drained for 15 sec (equivalent to 130 µl) into a prewarmed (37° C.) test tube containing the following incubation mixture in a final volume of 180 µl:3 µg of GC and buffer I, consisting of 0.1 mM [$\alpha^{32}$P] GTP (0.2 µCi); 0.1 mM cyclic GMP (cGMP); 30 mM triethanolamine hydrochloride (pH 7.4); 1 mM glutathione (GSH); 4 mM $MgCl_2$; 1.5 mM ethylene glycol bis (β-aminoethyl ether)-N,N' tetra acetic acid (EGTA) (to trap the calcium of the Tyrode's solution); and 0.1 mg/ml of bovine-y-globuline. The enzymatic formation of [$^{32}$P]cGMP proceeded for 1 minute at 37° C. The reaction was stopped by precipitation of unreacted GTP with 450 µl of zinc acetate (120 mM) and 500 µl of sodium carbonate (120 mM). [$^{32}$P]cGMP was isolated by chromatography on acid alumina. GC activity was calculated as nanomoles of cGMP formed per minute per milligram of GC, as described in Schultz, G. and E. Bohme, 1984, *Guanylate cyclase In Methods of Enzymatic Analysis*, Vol. 3, ed. H. U. Bergmeyer, Verlag Chemie, Weinheim, 379–389.

For the evaluation of the direct effect of 6-anilinoquinoline-5,8-quinone on GC in the presence of different thiols and sodium nitroprusside (SNP), 1 µg of GC was incubated with 100 µl of buffer II, which consisted of 0.1 mM [$\alpha^{32}$P]GTP (0.2 µCi); 0.1 mM cGMP; 30 mM triethanolamine hydrochloride (pH 7.4); 3 mM $MgCl_2$; 0.1 mM EGTA; 3 mM of a thiol, 6-anilinoquinoline-5,8-quinone (0.3–30 µM); and 100 µM SNP, as indicated.

This assay is reported in Mulsch, et al, "LY 835583 interferes with the release of endothelium-derived relaxing factor and inhibits soluble guanylate cyclase", J. Pharmacol. Exp. Ther. 247: 283–288, 1988. Other assays for GCI activity are reported in Schmidt et al, "LY835583: An Agent That Lowers Intracellular Levels of Cyclic Guanosine 3', 5'-Monophosphate", The Journal of Pharmacology and Experimental Therapeutics, Vol. 232, 3, 764–769.

EXAMPLES

The present invention is demonstrated with vivo data. Intraocular pressure (IOP) in Beagle dogs was measured tonometrically with a Digilab pneumotonometer. Specifically, IOP was measured before administration of any drug to obtain a baseline pressure (T=hours). Immediately after the baseline measurement drug was administered topically as a single drop of 25 microliter volume to one eye of each animal and vehicle in an equal volume to the contralateral eye in a masked fashion. IOP was determined again at various time points, i.e. 2, 4, 6 and 24 hours after drug/vehicle administration. The results of such test are reported in Table 2 below.

TABLE 2

| LY-83583 | | 0 h | 2 h | 4 h | 6 h | 24 h |
|---|---|---|---|---|---|---|
| 0.1% | T | 17.3* | 16.3 | 14.9 | 15.7 | 17.9 |
|  | C | 15.9 | 16.2 | 14.7 | 16.1 | 17.9 |
| 0.3% | T | 16.6 | 16.3 | 15.8 | 14.8 | 12.3* |
|  | C | 15.9 | 16.7 | 16.6 | 15.7 | 16.1 |
| 1.0% | T | 16.8 | 15.8 | 15.4* | 12.3* | 8.1* |
|  | C | 16.4 | 16.3 | 17.4 | 16.3 | 15.4 |

Intraocular pressure in Beagle dogs at various time points after administration of a single topical dose of LY-83583 to one eye (T) and vehicle to the contralateral eye (C). Pressure values are given in mm Hg. n=6 to 8. * p<0.05 vs. control.

Several modifications of the present invention may become readily apparent to those skilled in the art in light of the present disclosure. For example, this invention also provides therapy for congenital ocular hypertensive diseases, other than glaucoma, and is useful for treating ocular hypertensive episodes associated with ocular surgery and other invasive procedures. This invention also provides therapy for normal-tension glaucoma, i.e. it is useful for treating glaucoma which is not associated with ocular hypertension.

In view of the above, it is clear that the scope of the present invention should be interpreted solely on the basis of the following claims, as such claims are read in light of the disclosure.

What is claimed is:

1. A method of treating animals of the mammalian species, including humans, for the purpose of reducing intraocular pressure in the eye of the mammal, comprising the step of administering to the mammal an ophthalmic composition which comprises as its active ingredient one or more compounds having guanylate cyclase inhibition activity compounds selected from the group consisting of compounds represented by the formula:

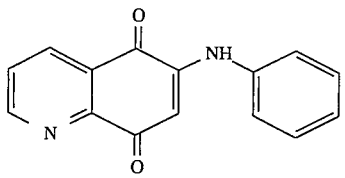

and pharmaceutically acceptable salts thereof.

2. The method of treatment of claim 1 wherein the composition is an ophthalmic solution adapted for administration to the eye of a mammal in the form of eye droplets.

3. The method of treatment of claim 1 wherein in the ophthalmic composition the concentration of the compound having guanylate cyclase inhibition activity is in the range of approximately 0.0001 to 1.0 percent weight by volume.

4. A method for providing neuroprotective effect to the eye of a mammal which comprises the step of administering to the mammal a pharmaceutical composition which comprises as its active ingredient one or more compounds having guanylate cyclase inhibition activity, wherein the compound having guanylate cyclase inhibition activity is selected from the group consisting of compounds represented by the formula:

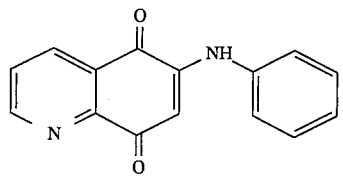

and pharmaceutically acceptable salts thereof.

5. The method of claim 4 wherein the composition contains approximately 0.0001 to 1.0 percent weight by volume of said compound having guanylate cyclase inhibition activity.

\* \* \* \* \*

UNITED STATES PATENT AND TRADEMARK OFFICE
CERTIFICATE OF CORRECTION

PATENT NO. : 5,602,143

DATED : February 11, 1997

INVENTOR(S) : Achim H. Krauss

It is certified that error appears in the above-identified patent and that said Letters Patent is hereby corrected as shown below:

Column 6, line 16; delete "LY 835583" and insert in place thereof --LY 83583--

Column 6, line 20; delete "LY 835583" and insert in place thereof --LY83583--.

Column 6, line 28 delete "vivo" and insert in place thereof --in vivo--

Signed and Sealed this

Nineteenth Day of August, 1997

Attest:

BRUCE LEHMAN

Attesting Officer

Commissioner of Patents and Trademarks